US005770717A

United States Patent [19]
Golemis et al.

[11] Patent Number: 5,770,717
[45] Date of Patent: Jun. 23, 1998

[54] NUCLEIC ACID ENCODING A STRESS-RESPONSIVE SUBUNIT OF HUMAN RNA POLYMERASE II

[75] Inventors: Erica A. Golemis, Oreland, Pa.; Vladimir Khazak, Princeton, N.J.; Joanne Estojak, Jenkintown, Pa.

[73] Assignee: Fox Chase Cancer Center, Philadelphia, Pa.

[21] Appl. No.: 376,157

[22] Filed: Jan. 20, 1995

[51] Int. Cl.$^6$ ............................ C12N 9/12; C12N 15/54
[52] U.S. Cl. .................. 536/23.2; 435/194; 536/24.1; 536/24.33; 536/24.31
[58] Field of Search .......................... 435/194; 536/23.2, 536/24.33, 24.1, 24.31

[56] References Cited

PUBLICATIONS

Abraham et al., 1992, Yeast 8:227–238.
Acker et al., 1993, Nucl. Acids Res. 21:5345–5340.
Gietz and Sugino, 1988, Gene 74:527–534.
Boeke et al., Meth. Enz. 154:164–175 (no date available).
Brent and Ptashne, 1984, Nature 312:612–615.
Brent and Ptashne, 1985, Cell 43:729–736.
Calabrasi and Chabner, in *The Pharmacological Basis of Therapeutics*, A.G. Gilman et al., eds., 1992 Pergamon Press, New York, pp. 1202–1263.
Cho et al., 1985, J. Biol. Chem. 260:15204–15210.
Choder and Young, 1993, Mol. Cell Biol. 13:6984–6991.
Choder, 1993, J. Bact. 175:6358–6363.
Dillon and Rosen, 1990, Biotechniques 9:298–300.
Edwards, 1991, J. Biol. Chem. 266:71–75.
Elledge et al., 1994, Cancer Research 54:3752–3757.
Fields and Song, 1989, Nature 340:245–246.
Georgeopoulos et al., 1993, Ann. Rev. Cell Biol. 9:601–634.
Gimeno et al., 1992, Cell 68:1078–1090.
Golemis et al., "Two Hybrid System/ Interaction Traps," in *Current Protocols in Molecular Biology*, Supp. 27, F.M. Ausubel et al., eds. John Wiley and Sons, New York pp. 13.14.1–13.14.27 (no date).
Golemis and Brent, 1992, Mol. Cell Biol. 12:3006–3014.
Gimeno and Fink, 1994, Mol. Cell Biol. 14:2100–2112.
Grenson et al., 1966, Biochem. Biophys. Acta 127:325–338.
Hoffman and Winston, 1987, Gene 57:267–272.
Kolodziej et al., 1990, Mol. Cell Biol. 10:1915–1920.
Kolodziej and Young, 1991, Meth. Enz. 194:508–519.
Love and King, 1994, British J. Cancer 69:743–748.
McKune, 1993, Yeast 9:295–299.
McKune and Woychik, 1994, Mol. Cell Biol. 14;4155–4159.
Pati and Weissman, 1989, J. Biol. Chem. 264:13114–13121.
Pati and Weissman, 1990, J. Biol. Chem. 265:8400–8403.
Samson et al., 1989, Cell 57:1045–1052.
Muhlrad et al., 1992, Yeast 8:79–82.
Sikorski and Hieter, 1989, Genetics 122:19–27.
Takahashi et al., 1994, Am. J. Clin. Path. 101:519–525.
Ulmasov and Guilfoyle, 1992, J. Biol. Chem. 267:23165–23169.
Wintzerith et al., 1992, Nucl. Acids Res. 20:910.
Young, 1991, Ann. Rev. Biochem. 60:689–715.
Gyuris et al., 1993, Cell 75:791–803.
Genexpress, Submitted 21 Feb. 1994 to EMBL/GENBANK/DDBJ Databases, Accession #730203.
Falb et al., *Mol. Cell. Biol.*, 12(9): 4093–4103, Sep. 1992.

*Primary Examiner*—Keith D. Hendricks
*Attorney, Agent, or Firm*—Janet E. Reed; Dann, Dorfman, Herrell, and Skillman

[57] ABSTRACT

An isolated nucleic acid is provided, which encodes a stress-responsive subunit of mammalian RNA polymerase II, RPB4. In a preferred embodiment, the human RPB4 subunit (hsRPB4) is provided. Also provided are oligonucleotides that specifically hybridize with the nucleic acid, the purified polypeptide encoded by the nucleic acid and antibodies immunologically specific for the polypeptide. These biological molecules are useful as markers of stress-related responses, which may correspond to the occurrence of malignant disease, and as therapeutic agents to modify resistance of a selected cell population to external stress conditions, such as that resulting from treatment of a patient with chemotherapeutic agents.

11 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
  ( A ) LENGTH: 753 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| GTGGCGCGCG | GCGGCGGGNC | GNATGCCGGC | GGGTGGCAGC | GATCCGCGNG | CTGGCGACGT | 60 |
| AGAGGAGGAC | GCCTCACAGC | TCATCTTTCC | TAAAGAGTTT | GAAACAGCTG | AGACACTTCT | 120 |
| AAATTCAGAA | GTTCATATGC | TTCTGGAACA | TCGAAAGCAG | CAGAATGAGA | GTGCAGAGGA | 180 |
| CGAACAGGAG | CTCTCAGAAG | TCTTCATGAA | AACATTAAAC | TACACAGCCC | GTTTCAGTCG | 240 |
| TTTCAAAAAC | AGAGAGACCA | TTGCCAGTGT | TCGTAGCTTG | CTACTCCAGA | AAAAGCTTCA | 300 |
| TAAGTTTGAG | TTGGCCTGTT | TGGCCAACCT | TTGCCCAGAG | ACTGCTGAGG | AGTCCAAGGC | 360 |
| TCTAATCCCA | AGCTTGGAGG | GACGGTTTGA | AGATGAGGAG | CTGCAGCAGA | TTCTTGATGA | 420 |
| TATCCAGACA | AAGCGCAGCT | TTCAGTATTA | ATCTCCAAAC | ATCACTGCTG | CTCGGAGAAA | 480 |
| CCACATCCCC | AGGCATAACA | CCACCTTCCC | ACTGTCTGGG | GCTGACTTGC | ACAGAAATTC | 540 |
| TGTTGAAGAC | AGGTGAGAAT | TCCTTTGGGA | GAAACAGCC | CAGCTTGGCG | TGGGGGTTAG | 600 |
| GTTGGTGTTT | CAAATATACT | CACAGGCCCA | GGTGACATGG | AATCTTGGGA | GCAGCCTTGT | 660 |
| GCAGGGGCAG | CCAGTGGCTT | CCTGAACGTG | CCTCTTCGAA | GTGTGAGATG | AGGGGTCACA | 720 |
| TAACCACACT | GTTGACTTCC | TTATTCCTGG | TTT | | | 753 |

( 2 ) INFORMATION FOR SEQ ID NO:2:

( i ) SEQUENCE CHARACTERISTICS:
    ( A ) LENGTH: 142 amino acids
    ( B ) TYPE: amino acid
    ( C ) STRANDEDNESS: Not Relevant
    ( D ) TOPOLOGY: Not Relevant ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

| Met | Pro | Ala | Gly | Gly | Ser | Asp | Pro | Arg | Ala | Gly | Asp | Val | Glu | Glu | Asp |
|---|---|---|---|---|---|---|---|---|---|---|---|---|---|---|---|
| 1 | | | | 5 | | | | | 10 | | | | | 15 | |

| Ala | Ser | Gln | Leu | Ile | Phe | Pro | Lys | Glu | Phe | Glu | Thr | Ala | Glu | Thr | Leu |
|---|---|---|---|---|---|---|---|---|---|---|---|---|---|---|---|
| | | | 20 | | | | | 25 | | | | | 30 | | |

| Leu | Asn | Ser | Glu | Val | His | Met | Leu | Leu | Glu | His | Arg | Lys | Gln | Gln | Asn |
|---|---|---|---|---|---|---|---|---|---|---|---|---|---|---|---|
| | | | 35 | | | | 40 | | | | | 45 | | | |

| Glu | Ser | Ala | Glu | Asp | Glu | Gln | Glu | Leu | Ser | Glu | Val | Phe | Met | Lys | Thr |
|---|---|---|---|---|---|---|---|---|---|---|---|---|---|---|---|
| | 50 | | | | | 55 | | | | | 60 | | | | |

| Leu | Asn | Tyr | Thr | Ala | Arg | Phe | Ser | Arg | Phe | Lys | Asn | Arg | Glu | Thr | Ile |
|---|---|---|---|---|---|---|---|---|---|---|---|---|---|---|---|
| 65 | | | | | 70 | | | | | 75 | | | | | 80 |

| Ala | Ser | Val | Arg | Ser | Leu | Leu | Leu | Gln | Lys | Lys | Leu | His | Lys | Phe | Glu |
|---|---|---|---|---|---|---|---|---|---|---|---|---|---|---|---|
| | | | | 85 | | | | | 90 | | | | | 95 | |

| Leu | Ala | Cys | Leu | Ala | Asn | Leu | Cys | Pro | Glu | Thr | Ala | Glu | Glu | Ser | Lys |
|---|---|---|---|---|---|---|---|---|---|---|---|---|---|---|---|
| | | | | 100 | | | | | 105 | | | | | 110 | |

| Ala | Leu | Ile | Pro | Ser | Leu | Glu | Gly | Arg | Phe | Glu | Asp | Glu | Glu | Leu | Gln |

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |
| Gln | Ile | Leu | Asp | Asp | Ile | Gln | Thr | Lys | Arg | Ser | Phe | Gln | Tyr |     |     |
|     |     | 130 |     |     |     | 135 |     |     |     |     | 140 |     |     |     |     |

(2) INFORMATION FOR SEQ ID NO:3:

(i) SEQUENCE CHARACTERISTICS:
        (A) LENGTH: 775 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:3:

```
ACTCTGCCTG CCTACCTGGT CTGGGAAGAT GTTCTACCAT ATCTCCTAG AGCACGAAAT      60
CCTGCTGCAC CCGCGCTACT TCGGCCCCAA CTTGCTCAAC ACGGTGAAGC AGAAGCTCTT     120
CACCGAGGTG GAGGGGACCT GCACAGGGAA GTATGGCTTT GTAATTGCTG TCACCACCAT     180
TGACAATATT GGTGCTGGTG TGATCCAGCC AGGCCGAGGC TTTGTCCTTT ATCCAGTTAA     240
GTACAAGGCC ATTGTTTTCC GGCCATTTAA AGGGGAGGTC GTGGATGCTG TTGTCACTCA     300
GGTCAACAAG GTTGGACTCT TCACAGAAAT TGGGCCCATG TCTTGCTTCA TCTCTCGACA     360
TTCCATCCCT TCAGAGATGG AGTTTGATCC TAACTCCAAC CCACCATGTT ACAAGACAAT     420
GGATGAGGAT ATTGTGATTC AGCAGGACGA TGAGATCCGC TTAAAGATTG TGGGGACCCG     480
TGTGGACAAG AATGACATTT TTGCTATTGG CTCCCTGATG GACGATTACT GGGGCTTGT     540
AAGCTGAGCC TGGTGGCCTC CTACCCTTGG TCCTACTCTA GGAAGTGTGA TTGTCACACT     600
TATCATGTTG TCCAGAGGTC CAGTCTGGCT GCTGTTGTGG AGGCAAGGAA GGCAACTCAT     660
CCCAGAAGGC ATCTGGTGCT TCTTGTAGCT TAACTACTGC CTCCTCATTT TTCAGTATGT     720
GTTCTAAGTA TAAAAAGTCC TTTGGTTCTC AAAAAAAAAA AAAAAAAAA AAAAA           775
```

(2) INFORMATION FOR SEQ ID NO:4:

(i) SEQUENCE CHARACTERISTICS:
        (A) LENGTH: 172 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:4:

| Met | Phe | Tyr | His | Ile | Ser | Leu | Glu | His | Glu | Ile | Leu | Leu | His | Pro | Arg |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Tyr | Phe | Gly | Pro | Asn | Leu | Leu | Asn | Thr | Val | Lys | Gln | Lys | Leu | Phe | Thr |
|     |     |     | 20 |     |     |     |     | 25 |     |     |     |     | 30 |     |     |
| Glu | Val | Glu | Gly | Thr | Cys | Thr | Gly | Lys | Tyr | Gly | Phe | Val | Ile | Ala | Val |
|     |     |     | 35 |     |     |     |     | 40 |     |     |     |     | 45 |     |     |
| Thr | Thr | Ile | Asp | Asn | Ile | Gly | Ala | Gly | Val | Ile | Gln | Pro | Gly | Arg | Gly |
|     |     | 50 |     |     |     |     | 55 |     |     |     |     | 60 |     |     |     |
| Phe | Val | Leu | Tyr | Pro | Val | Lys | Tyr | Lys | Ala | Ile | Val | Phe | Arg | Pro | Phe |
| 65 |     |     |     |     | 70 |     |     |     |     | 75 |     |     |     |     | 80 |

|     |     |     |     |     |     |     |     |     |     |     |     |     |     |     |
| --- | --- | --- | --- | --- | --- | --- | --- | --- | --- | --- | --- | --- | --- | --- |
| Lys | Gly | Glu | Val | Val<br>85 | Asp | Ala | Val | Val | Thr<br>90 | Gln | Val | Asn | Lys | Val<br>95 | Gly |
| Leu | Phe | Thr | Glu<br>100 | Ile | Gly | Pro | Met | Ser<br>105 | Cys | Phe | Ile | Ser | Arg<br>110 | His | Ser |
| Ile | Pro | Ser<br>115 | Glu | Met | Glu | Phe | Asp<br>120 | Pro | Asn | Ser | Asn | Pro<br>125 | Pro | Cys | Tyr |
| Lys | Thr<br>130 | Met | Asp | Glu | Asp | Ile<br>135 | Val | Ile | Gln | Gln | Asp<br>140 | Asp | Glu | Ile | Arg |
| Leu<br>145 | Lys | Ile | Val | Gly | Thr<br>150 | Arg | Val | Asp | Lys | Asn<br>155 | Asp | Ile | Phe | Ala | Ile<br>160 |
| Gly | Ser | Leu | Met | Asp<br>165 | Asp | Tyr | Leu | Gly | Leu<br>170 | Val | Ser |     |     |     |     |

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (iv) ANTI-SENSE: NO (xi) SEQUENCE DESCRIPTION: SEQ ID NO:5:

| Asn<br>1 | Ser | Ala | Arg | Gly<br>5 | Gly | Thr | Leu | Pro | Ala<br>10 | Tyr | Leu | Val | Trp | Glu<br>15 |

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GGGCAATTGG CGTCGAGAAT GTTTTTTATT AAAGACCTTT C        41

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

CCCCTCGAGA TGTTGCGGAG TAACAAGTGA TTAAATA        37

(2) INFORMATION FOR SEQ ID NO:8:

(i) SEQUENCE CHARACTERISTICS:

(A) LENGTH: 39 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGGCAATTGT CGGGAAAAAT GAATGTTTCT ACATCAACC 39

(2) INFORMATION FOR SEQ ID NO:9:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CCCCTCGAGA TACAGTTATT AATAGAGTGT TTCTAGG 37

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GCGGATCCGC TCCTTTCCCT GCTCTATGCC 30

(2) INFORMATION FOR SEQ ID NO:11:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

GCAGATATGG TAGAACATTC TCAGAAATTG AG 32

(2) INFORMATION FOR SEQ ID NO:12:

(i) SEQUENCE CHARACTERISTICS:
(A) LENGTH: 36 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:12:

ACTTGGGGCT TGTAAGCTGA TCACTTGTTA CTCCGC 36

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:13:

GCGTCGACGA GGGGGAATAG ATTCTTTAGC 30

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:14:

AGCAAGTTGG GGCCGAAG 18

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:15:

CAGTTCATCC GGACTCAGGA CTCCG 25

NUCLEIC ACID ENCODING A STRESS-RESPONSIVE SUBUNIT OF HUMAN RNA POLYMERASE II

FIELD OF THE INVENTION

This invention relates to the diagnosis and treatment of neoplastic disease and other pathological conditions involving stress responses. More specifically, this invention provides novel nucleic acid molecules, proteins and antibodies useful for detection and/or regulation of cellular resistance to environmental stress, particularly as induced by toxic substances such as anti-neoplastic drugs.

BACKGROUND OF THE INVENTION

Cells possess numerous mechanisms designed to resist damage from external environmental sources. Many of these mechanisms are highly evolutionarily conserved, and some, including the induction of heat shock proteins (see Georgeopoulos et al., Ann. Rev. Cell Bio. 9:601–634, 1993) and other detoxifying enzymes (see Calabresi & Chabner, in *The Pharmacological Basis of Therapeutics*, A. G. Gilman et al., eds., 1992, Pergamon Press, New York, pp 1202–1263) have been extensively characterized. These so-called stress-related proteins accumulate in response to a variety of environmental conditions including exposure to toxic agents, hyperthermia, starvation, hypoxia and oxidative stress. Certain stress-related proteins have been found associated with malignant cell growth, particularly breast cancer (see, e.g., Elledge et al., Cancer Research 54:3752–3757, 1994; Takahashi et al., Am. J. Clin. Pathol. 101:519–525, 1994; Love & King, British J. Cancer 69:743–748). The appearance of stress proteins in malignant cells is not surprising, inasmuch as cellular transformation during the development of cancer involves multiple alterations in the normal pattern of cell growth regulation, which is likely to induce one or more stress conditions. Thus, the presence or elevation of certain stress proteins in a cell or tissue can serve as an early diagnostic indicator of malignancy.

Cancers are generally treated by chemotherapy or radiation therapy. The goal of such therapy is to selectively target and eliminate transformed malignant cells, with a minimum of damage to normal cells. Because it not yet possible to completely target cancerous tissues, this process inevitably causes substantial damage to normal tissues. One approach to improving chemotherapy is to selectively enhance or diminish the ability of a defined population of cells to resist the damage associated with drug treatment. Such therapy may be accomplished by means of regulating stress proteins in the selected cell population, to render them either more or less resistant to therapeutic cancer-treating agents. It is apparent from the foregoing discussion that purified, characterized human stress-related proteins may be utilized for a variety of diagnostic and therapeutic purposes. Stress proteins that are found to be associated with malignant cell growth can operate as diagnostic indicators of malignant disease. Additionally, regulation of such stress proteins in a selected cell population can be used as an adjunct to chemotherapy or radiation therapy, to render the normal cell population more resistant to such therapeutic agents. Alternatively, expression of stress proteins may be regulated to diminish expression, in order to render the malignant cell population less resistant to anti-cancer drugs. Accordingly, it is advantageous to isolate and purify novel stress-related proteins from human sources for use in human diagnostics and therapeutics.

Recently, a novel mechanism of stress protection has been identified in yeast, in which transcriptional complexes are protected during stress by the selective association of two polymerase subunits (RPB7 and RPB4) with the larger RNA polymerase II complex. This mechanism is described hereinbelow.

The yeast (*Saccharomyces cerevisiae*) RNA polymerase II has been the best characterized of, and serves as a prototype for, eukaryotic RNA polymerases. Yeast RNA polymerase II (sometimes referred to herein as "pol II") is a complex of up to 12 protein subunits (RPB1-12) ranging from 10–220 kDa in size. In actively growing yeast, approximately 20% of RNA pol II is purified as a species containing all 12 subunits, while 80% is purified as a species lacking a subcomplex made up of the RPB4 and RPB7 subunits (Edwards, J. Biol. Chem. 266:71–75, 1991). Significantly, in yeasts that are in stationary phase (a stress-related condition), the relative proportion of complexes alters, with virtually all RNA pol II containing the RPB4/RPB7 subcomplexes (Choder & Young, Mol. Cell. Bio. 13:6984–6991, 1993). Several lines of experimentation have indicated that the two species possess substantially different transcriptional activities. In vitro experiments have shown, that while both species of pol II are indistinguishable in promoter-independent initiation assays, pol II lacking the RBP4/RBP7 subcomplex is inactive in promoter-directed initiation assays, unless a strong transcriptional activator (such as GAL4-VP16) is bound at an adjacent binding site (Edwards, 1991, supra).

Yeast strains with null alleles for RPB7 (rpb7⁻ strains) are inviable under normal conditions (McKune, Yeast 9:295–299, 1993). By contrast, Yeast strains with null alleles for RPB4 (rpb4⁻ strains) show little phenotype under normal growth conditions, but are inviable under conditions of temperature stress, and lose viability much more rapidly than wild type yeast when kept at stationary phase (Choder & Young, 1993, supra). In comparison, yeast made to overexpress RPB4 grow significantly better as they approach stationary phase than do yeast expressing normal levels of RPB4. This result suggests that RPB4 might play a rate-limiting role in transcription (Choder, J. Bact. 175:6358–6363, 1993). In rpb4⁻ yeast, mRNA synthesis declines rapidly after heat shock or during shift to stationary phase growth, relative to RPB4⁺ (Choder & Young, 1993, supra). Moreover, RPB7 cannot be immunoprecipitated with the pol II complex in rpb4⁻ yeast (Kolodziej et al., Mol. Cell. Bio. 10:1915–1920, 1990), suggesting that RPB4 is necessary for a stable association of RPB7 with the complex.

The above-described results suggest that the RPB4/RPB7 complex increases the resistance of RNA polyermerase II to stress, supplementing previously defined stress-resistance, such as that provided by heat shock proteins. The results also indicate that RPB4 is the stress-related partner of the RPB4/RPB7 complex. However, to date, published studies on human pol II have offered little evidence that the RPB4/RPB7 system is evolutionarily conserved through humans. No RPB4-like subunit has been detected as a component of human purified pol II (see Young, Ann. Rev. Biochem. 60:689–715, 1991).

It is an object of the present invention to provide a purified nucleic acid molecule of mammalian, preferably human, origin that encodes the stress-related protein RPB4, and therefrom to provide isolated and purified RPB4 protein. The human RPB4-encoding nucleic acid and RPB4 protein (sometimes referred to herein as "hsRPB4") and related genes and proteins from other mammalian species will find a variety of utilities in diagnosis and therapy of various cancers, and may also find utility in therapy of other stress-related diseases. It is a further object of the present invention to provide derivatives of the RPB4-encoding nucleic acids of the invention, such as various oligonucleotides and nucleic acid fragments, for use as probes or reagents to control expression of genes encoding RPB4. It is a further object of the invention to provide isolated antibodies immunologically specific for RPB4 proteins, for the purpose of identifying and quantitating RPB4 in selected cells and tissues.

SUMMARY OF THE INVENTION

In accordance with the present invention, an isolated nucleic acid molecule is provided, which encodes the stress-related RPB4 subunit of a mammalian, preferably human, RNA polymerase II. Isolated RPB4 proteins encoded by the nucleic acids of the invention are also provided, as well as antibodies immunologically specific for those proteins.

According to one aspect of the present invention, an isolated nucleic acid molecule that includes a sequence encoding an RPB4 subunit of mammalian RNA polymerase II is provided. The nucleic acid molecule may be single- or double-stranded DNA or RNA. oligonucleotides are also provided (preferably 10–100 bases long), which specifically hybridize with selected portions of the RPB4-encoding sequence of the nucleic acid molecule described above (e.g., a portion containing a translation initiation site).

According to one embodiment of the present invention, the nucleic acid molecules of the invention encode a polypeptide having an amino acid sequence substantially the same as Sequence I.D. No. 2, set forth herein. In a preferred embodiment, the nucleic acid molecule comprises a sequence which is Sequence I.D. No. 1 or an RNA equivalent thereof.

According to another aspect of the present invention an isolated and purified protein is provided, which is an RPB4 subunit of mammalian RNA polymerase II. This protein preferably comprises an amino acid sequence substantially the same as Sequence I.D. No. 2, set forth herein.

According to another aspect of the present invention, antibodies are provided which are immunologically specific for an RPB4 subunit of mammalian RNA polymerase II. The antibodies may be polyclonal or monoclonal, and are preferably immunologically specific for a human RPB4 subunit.

Various terms relating to the biological molecules of the present invention are used hereinabove and also throughout the specifications and claims. The term "substantially the same" is defined in detail in the description set forth herein below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., RPB4), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids, proteins and antibodies of the present invention are useful for diagnosis and therapy of various cancers and other stress-related diseases. These molecules may be used as probes for detection of stress responses in cells or tissues, or as reagents to increase or decrease production of RPB4 in a selected cell population or target tissue.

DETAILED DESCRIPTION OF THE INVENTION

Experiments with the yeast RPB7 gene have shown that overexpression of its "partner" subunit, RPB4, is sufficient to support more vigorous growth in yeast growing under poor nutrient conditions (Choder, 1990 supra). However, a mammalian RPB7/RPB4 complex heretofore not been identified. In accordance with the present invention, it has now been discovered that the human RNA polymerase II indeed comprises an RPB7/RPB4 complex such as that found in yeast.

Using a screen to identify human genes that promote pseudohyphal conversion in the yeast, Saccharomycia cereviciae, a cDNA clone was obtained that encodes a human homolog of RPB7 (hsRPB7). As described in greater detail in Example 1, overexpression of yeast RPB7 in a comparable strain background caused more cell elongation than overexpression of hsRPB7. HsRPB7 sequence and function were found to be strongly conserved with its yeast counterpart, since its expression was capable of rescuing deletion of the essential RPB7 gene in yeast grown in moderate temperatures. Additionally, immunoprecipitation of RNA polymerase II from yeast cells containing hsRPB7 revealed that the hsRPB7 assembles the complete set of eleven other yeast subunits.

In contrast to its behavior at normal temperatures, at temperature extremes and during maintenance at stationary phase, hsRPB7-containing yeast cells lost viability rapidly, which is a stress-sensitive phenotype reminiscent of that associated with deletion of yeast RPB4 subunits with which yeast RPB7 normally complexes. Further analysis revealed that, although hsRPB7 and yeast RPB4 interacted, the association was of lower affinity than the yeast—yeast RPB4/RPB7 interaction. This result suggested a probable mechanism for the failure of hsRPB7 to fully function in yeast cells at high and low temperature extremes and in stationary phase.

As described above, prior to the present invention, a mammalian RPB4/RPB7 complex had not been identified. HsRPB7 was isolated as part of a screen involving pseudohyphal conversion in yeast. Thereafter, human RPB4 (hsRPB4) was isolated, not by conventional library screening, but instead through the use of a screening technique designed to identify proteins that associate with hsRPB7. This screening methodology is referred to herein as the "interaction trap," and is described in detail in Golemis et al., "Two Hybrid System/Interaction Traps," in *Current Protocols in Molecular Biology*, Supp. 27, F. M. Ausubel et al., Eds. 1994, John Wiley & Sons, New York pp. 13.14.1–13.14.27. The specific procedures for identifying hsRPB4 using the interaction trap screening method is described in greater detail in Example 1.

The interaction trap screen led to the identification of cDNA clones which together comprise the sequence set forth as Sequence I.D. No. 1 herein. Sequence I.D. No. 1 is approximately 40% identical to the coding sequence of the gene encoding the yeast RPB4 protein. The amino acid sequence deduced from Sequence I.D. No. 1 is set forth herein as Sequence I.D. No. 2. Sequence I.D. No. 2 is 31% identical to, and 55% similar to the amino acid sequence of yeast RPB4 over a region of about 142 amino acids. These levels of amino acid homology are statisically significant for the coding amino acid sequence. However, the DNA homology is not significant, which could explain why conventional hybridization techniques using yeast RPB4 probes would not be successful in isolating their mammalian or human counterparts. Amino acid Sequence I.D. No. 2 also contains statistically significant homology to another protein in the GENBANK database, which is encoded by a chicken gene of unknown functions that may also play an RPB4-like role (however, the chicken sequence is more divergent than the yeast/human sequences and so may merely represent a related transcription factor). It is believed that Sequence I.D. No. 1 constitutes a full-length hsRPB4 clone as it contains a suitable methionine for initiation of translation. This cDNA is approximately 1.8 kb in length. Northern analysis of a human multi-tissue RNA blot (Clontech MTNI) with the hsRPB4 probe suggests a full-length transcript of approximately 1.8–2.1 kb. A second transcript of approximately 4 kb was also observed, which may represent an alternative splice or initiation site, or a related gene.

Although the human RPB4 is described and exemplified herein, this invention is intended to encompass nucleic acid sequences and proteins from other species that are sufficiently similar to be used interchanageably with hsRPB4-encoding nucleic acids and proteins for the diagnostic and therapeutic purposes described below. Because of the high degree of conservation of RNA polymerase II among species (see Young, 1991, supra) it will be appreciated by those skilled in the art that, even though the human-yeast RPB4 homology is low, RPB4 nucleic acids and proteins from a variety of mammalian species should possess a sufficient degree of homology with hsRPB4 so as to be interchangeably useful with hsRPB4 in such diagnostic and therapeutic applications. Accordingly, the present invention is drawn to mammalian RPB4 nucleic acids and proteins, preferably to RPB4 of primate origin, and most preferably to RPB4 of human origin. Accordingly, when the term "hsRPB4 (protein or nucleic acid) of the invention" is used herein, it is intended to emcompass mammalian RPB4 nucleic acids and proteins falling within the confines of homology set forth below, of which hsRPB4 is an exemplary member.

The human RPB4 cDNA having Sequence I.D. No. 1 described above was identified by repeated interaction trap screening for proteins capable of interacting with human RPB7. Allelic variants and natural mutants of Sequence I.D. No. 1 are likely to exist within the human genome and within the genomes of other mammalian species. Because such variants are expected to possess certain differences in nucleotide and amino acid sequence, this invention provides an isolated nucleic acid molecule and an isolated RPB4 protein having at least about 50–60% (preferably 60–80%, most preferably over 80%) sequence homology in the coding region with the nucleotide sequence set forth as Sequence I.D. No. 1 (and, preferably, specifically comprising the coding region of sequence I.D. No. 1), and the amino acid sequence of Sequence I.D. No. 2. Because of the natural sequence variation likely to exist among RPB4 proteins and nucleic acids encoding them, one skilled in the art would expect to find up to about 40–50% sequence variation, while still maintaining the unique properties of the RPB4 protein of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. the structure and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") are used.

I. Preparation of nucleic acid molecules, RPB4 proteins and antibodies thereto

A. Nucleic Acid Molecules

Nucleic acid molecules encoding RPB4 proteins of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucletoides may be prepared by the phosphoramadite method employed in the Applied Biosystems 38A DNA Synthesizer or similar devices. The resultant construct may be purified according to high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2-kb double-stranded DNA molecule may be synthesized as several smaller segments of appropriate complementarily. Complementary segments thus produced may be annealed such that each segment possesses appropriate cohesive termini for attachment of an adjacent segment. Adjacent segments may be ligated by annealing cohesive termini in the presence of DNA ligase to construct an entire 2-kb double-stranded molecule. A synthetic DNA molecule so constructed may then be cloned and amplified in an appropriate vector.

Nucleic acid sequences encoding RPB4 may be isolated from appropriate biological sources using methods known in the art. In a preferred embodiment, a cDNA clone is isolated from an expression library of human origin. In an alternative embodiment, human genomic clones encoding RPB4 may be isolated. Alternatively, cDNA or genomic clones encoding RPB4 from other mammalian species may be obtained.

In accordance with the present invention, nucleic acids having the appropriate level sequence homology with the protein coding region of Sequence I.D. No. 1 may be identified by using hybridization and washing condition of appropriate stringency. For example, hybridizations may be performed, according to the method of Sambrook et al., using a hybridization solution comprising: 5×SSC, 5×Denhardt's reagent, 1.0% SDS, 100 μg/ml denatured, fragmented salmon sperm DNA, 0.05% sodium pyrophosphate and up to 50% formamide. Hybridization is carried out at 37°–42° C. for at least six hour. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42°–65° in 1×SSC and 1% SDS, changing the solution every 30 minutes.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

RPB4-encoding nucleic acid molecules of the invention include CDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting RPB4 genes in test samples of potentially malignant cells or tissues, e.g. by PCR amplification, or for therapy as regulators of gene expression.

B. Proteins

A full-length RPB4 protein of the present invention may be prepared in a variety of ways, according to known methods. The protein may be purified from appropriate sources, e.g., human or animal cultured cells or tissues, by immunoaffinity purification. However, due to the difficulties inherent in purifying RPB4 from the RNA pol II complex, conventional purification techniques are not preferred in the present invention.

The availability of nucleic acids molecules encoding RPB4 enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of RPB4 may be produced by expression in a suitable procaryotic or eucaryotic system. For example, part or all of a DNA molecule, such as the cDNA having Sequence I.D. No. 1, may be inserted into a plasmid vector adapted for expression in a bacterial cell, such as *E. coli*, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences.

The RPB4 protein produced by gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The RPB4 proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward RPB4 may be prepared according to standard methods. In a preferred embodiment, monoclonal antibodies are prepared, which react immunospecifically with various epitopes of RPB4. Monoclonal antibodies may be prepared according to general methods of Köhler and Milstein, following standard protocols. Polyclonal or monoclonal antibodies that immunospecifically interact with RPB4 can be utilized for identifying and purifying such proteins. For example, antibodies may be utilized for affinity separation of proteins with which they immunospecifically interact. Antibodies may also be used to immuoprecipitate proteins from a sample containing a mixture of proteins and other biological molecules. Other uses of anti-RPB4 antibodies are described below.

II. Uses of hsRPB4-Encoding Nucleic Acids, hsRPB4 Proteins and Antibodies Thereto Stress proteins have received a great deal of attention as potential prognostic indicators of neoplastic disease and as therapeutic agents to be used for a variety of purposes in cancer chemotherapy. As a stress-related protein intimately involved in regulation of transcription, hsRPB4 and related proteins from other mammalian species promise to be particularly useful diagnostic and therapeutic agents.

A. HsRPB4-Encoding Nucleic Acids

HsRPB4-encoding nucleic acids may be used for a variety of purposes in accordance with the present invention. For diagnosing malignant cell growth or for otherwise monitoring stress responses in vitro or in vivo, hsRPB4-encoding DNA, RNA, or fragments thereof may be used as probes to detect the presence of and/or expression of genes encoding hsRPB4. These probes may also be used for monitoring the assembly of RNA polymerase II for further assessment of this complex polypeptide in cells subjected to various environmental conditions. Methods in which hsRPB4-encoding nucleic acids may be utilized as probes for such assays include, but are not limited to: (1) In situ hybridization; (2) Southern hybridization (3) Northern hybridization; and (4) assorted amplification reactions such as polymerase chain reactions (PCR).

The hsRPB4-encoding nucleic acids of the invention may also be utilized as probes to identify related genes either from humans or from other species. As is well-known in the art, hybridization stringencies may be adjusted to allow hybridization of nucleic acid probes with complementary sequences of varying degrees of homology. Thus, hsRPB4-encoding nucleic acids may be used to advantage to identify and characterize other genes of varying degrees of relation to hsRPB4, thereby enabling further characterization of the transcription apparatus of different species.

Nucleic acid molecules, or fragments thereof, encoding hsRPB4 may also be utilized to control the expression of RPB4, thereby regulating the resistance of a selected cell population to external stress conditions, such as chemotherapeutic agents used to treat cancer. In one embodiment, the nucleic acid molecules of the invention may used to reduce or prevent expression of RPB4 in a population of malignant cells, thereby rendering those cells less resistant to the toxic effects of chemotherapeutic agents or radiation therapy. In this embodiment, antisense oligonucleotides are employed which are targeted to specific regions of RPB4-encoding genes that are critical for gene expression. The use of antisense oligonucleotides to reduce or eliminate expression of a pre-determined gene is known in the art. In a preferred embodiment, such antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, overexpression of RPB4 is induced in a target population of normal cells to increase their resistance to chemotherapeutic agents being used to treat a patient having neoplastic disease. For example, bone marrow toxicity is the main dose-limiting factor for many commonly used anti-cancer drugs. The ability to impart drug resistance selectively to bone marrow stem cells would improve cancer therapy because it would enable dosages of various chemotherapeutic agents to be increased, thereby enhancing efficacy of the treatment without compromising viability of hematopoietic progenitor cells. Nucleic acids encoding RPB4 may be utilized in this regard by genetically transforming the hematopoietic cells with the nucleic acid for the purpose of producing more RPB4 and thereby conferring additional stress tolerance. Hematopoietic progenitor cells from bone marrow or proiferal blood should be particularly amenable targets for such transformation protocols, since they can be treated ex vivo during the course of a normal autologous stem cell transplantation procedure.

As described above, RPB4-encoding nucleic acids are also used to advantage to produce large quantities of substantially pure RPB4 protein, or selected portions thereof. The protein is thereafter used for various diagnostic and therapeutic purposes, as described below.

B. HsRPB4 Protein and Antibodies

Purified hsRPB4 or fragments thereof, may be used to produce polyclonal or monoclonal antibodies which also may serve as sensitive detection reagents for the presence and accumulation of RPB4 (or complexes containing RPB4) in culture cells or tissues from living patients (the term "patients" refers to both humans and animals). Recombinant techniques enable expression of fusion proteins containing part or all of the hsRPB4 protein. The full length protein or fragments of the protein may be used to advantage to generate an array of monoclonal antibodies specific for various epitopes of the protein, thereby potentially providing even greater sensitivity for detection of the protein in cells or tissue.

Polyclonal or monoclonal antibodies immunologically specific for hsRPB4 may be used in a variety of assays designed to detect and quantitate the protein, which may be useful for rendering a prognosis as to a malignant disease. Such assays include, but are not limited to: (1) flow cytometric analysis; (2) immunochemical localization in RPB4 in cultured cells or tissues; and (3) immunoblot analysis (e.g., dot blot, Western blot) of extracts from various cells and tissues. Additionally, as described above, anti-RPB4 can be used for purification of RPB4 (e.g., affinity column purification, immunoprecipitation).

Anti-RPB4 antibodies may also be utilized as therapeutic agents to block the normal functionality of RPB4 in a target cell population, such as a tumor. Thus, similar to the antisense oligonucleotides described above, anti-RPB4 antibodies may be delivered to a target cell population by methods known in the art (i.e. through various lipophilic carriers that enable delivery of the compound of interest to the target cell cytoplasm) where the antibodies may interact with intrinsic RPB4 to render it nonfunctional (e.g., by preventing its assembly into RNA polymerase II).

From the foregoing discussion, it can be seen that RPB4-encoding nucleic acids and RPB4 proteins of the invention can be used to detect RPB4 gene expression and protein accumulation for purposes of assessing the stress status of a cell or tissue sample, which is often corrlelatable with metastatic cellular proliferation in various cancers, such as breast cancer. It is expected that these tools will be particularly useful for diagnosis and prognosis of human neoplastic disease. Potentially of greater significance, however, is the utilty of RPB4-encoding nucleic acids, proteins and antibodies as therapeutic agents to increase or supress the resistance of a selected cell population to environmental stress conditions such as hyperthermia, oxidative stress, starvation or exposure to toxic agent such as chemotherapeutic agents used in treatment of cancer.

Although the compositions of the invention have been described with respect to human diagnostics and therapeutics, it will be apparent to one skilled in the art that these tools will also be useful in animal and cultured cell experimentation with respect to various malignancies and/or other stress-related conditions. As diagnostic agents they can be used to monitor the effectiveness of potential anti-cancer agents on cellular proliferation in vitro, and/or the development of neoplasms or malignant diseases in animal model systems. As therapeutics, they can be used either alone or as adjuncts to other chemotherapeutic drugs in animal models and veterinary applications to improve the effectiveness of such anti-cancer agents.

The following Example is provided to describe the invention in further detail. This Example is intended to illustrate and not to limit the invention.

EXAMPLE 1

Isolation and Characterization of a Nucleic Acid Molecule Encoding Human RPB4

In this Example, we describe the isolation of a human RPB4 homolog, hsRPB4. In order to obtain hsRPB4, we first isolated a human analog of RPB7, hsRPB7, through a genetic screen in yeast, similar to that recently described by Gimeno & Fink, Mol. Cell. Biol. 14:2100–2112 (1994). The isolation of hsRPB7, and thereafter hsRPB4, is described in detail below.

METHODS

Bacteria and Yeast Strains. The *E. coli* strain DH5αF' [F'/endA1 hsdR17(rK–mK+)supE44 thi-1 recA1 gyrA (Nalr) relA1 D(lacZYA-argF) U169 (f80lacD(lacZ)M15)] was used as a host for all cloning constructions. The *S. cerevisiae* strain CGx74 [MAT a/a trp1::his6/trp1::his6] similar to CGx3l (Gimeno et al., Cell 68:1077–1090, 1992), and congenic with the S1278b genetic background (Grenson et al., Biochem. Biophys. Acta 127:325–338, 1966) was used in the library screen in which hsRPB7 was isolated. The yeast strain WY-7 [MATa/a ura3-52/ura3-52 his3D200/his3D200 leu2-3,112/leu2-3 ,112 lys2D201/lys2D201 ade2/ade2 RPB7/rpb7D1::LEU2] (McKune et al., Yeast 9:295–299, 1993) and its haploid derivative WY-73 [MATa ura3-52 his3D200 leu2-3 ,112 lys2D201 ade2 rpb7D1::LEU2 [pRP729] were used in complementation studies. WY-76, WY-77 and WY-78 were derivatives of WY-73 that contain an additional plasmid, pRS413, pRP730, or pRP731, respectively. WY-74 [MATa ura3-52 his3D200 leu2-3 ,112 lys2D201 ade2 rpb7D1::LEU2 [pRP730] and WY-75 [MATa ura3-52 his3D200 leu2-3 ,112 lys2D201 ade2 rpb7D1::LEU2 [pRP731] were obtained after 5-fluoroorotic acid selection against the URA3 plasmid pRP729. The yeast strains EGY48 [MATa ura3 his3 trp131exAop-leu2] (Gyuris et al., Cell 75:791–803, 1993) and EGY191 [MATa ura3 his3 trp131exAop-leu2] were used for immunoprecipitation studies and two hybrid assays. Yeast cells were grown either on YPD rich medium, or on complete minimal medium lacking combinations of amino acids to select for the presence of plasmids according to standard methods, except as noted below.

Library Screen and Assessment of Pseudohyphal Growth. Oligo(dT) primed cDNA prepared from mRNA from actively proliferating HeLa cells was cloned into the galactose inducible yeast expression vector JG4-4 (2 μ, TRP1). The resulting library was transformed into the yeast strain CGx74 by the procedure of Schiestl and Gietz (Curr. Genet. 16:339–346, 1989), and 3×10$^6$ primary transformants were obtained on trp$^-$ glucose plates. Colonies were scraped off the plates and pooled in a 50 ml Falcon tube. A solution of 65% glycerol, 10 mM Tris-HCl pH 7.5, and 10 mM MgCl2 in volume equivalent to the packed cell volume was added, and the resulting slurry stored in 1 ml aliquots at –70° C. For the screen, an aliquot was thawed, 250 μl of slurry diluted to OD$_{600}$ of 0.6 in YPD medium, and grown overnight at 30° C. The following morning the overnight culture had an OD$_{600}$ of 3.0: this culture was rediluted to OD$_{600}$ 0.15 into YP medium with 2% galactose and 1% raffinose, and grown for 5 hours (approx. 1 doubling) at 30° C. Cells were pelleted at 1200 g for 5 minutes, washed 2× with distilled water, and plated at a density of $^-$3000–5000 cells/10 cm plate of SLAHGR medium (6.7 g/liter Difco Yeast Nitrogen Base without amino acids and ammonium sulfate [Difco Laboratories], 0.2 mM L-histidine hydrochloride, 0.05 mM ammonium sulfate, 20% Difco agar, 2% galactose, 1% raffinose), and grown at 30° C. for 2–3 days. Plates were then scanned using a Wild dissecting microscope at 25×, and colonies with enhanced formation of pseudohyphal projections were picked to a master plate. Library DNA was isolated from these colonies (Hoffman & Winston, Gene 57:267–272, 1987), transformed into *E. coli*, and retransformed into fresh CGx74: cDNAs that again enhanced pseudohyphal formation were chosen for further analysis.

For subsequent assays of formation of pseudohyphae, CGx74 yeast were transformed with plasmids as described in the Results, plated to trp- glucose to select transformants, then restreaked to SLAHGR plates. Pseudohyphae were photographed at 24–72 hours after streaking.

Sequence Analysis. Both strands of the RPB7hs gene were sequenced using oligonucleotide primers to the JG4-4 vector and to internal hsRPB7 sequence in combination with the Sequenase system (United States Biochemical). Database searching was performed using the BLAST algorithm (Altschul et al., J. Mol. Biol. 215:403–410, 1990) and sequence analysis was carried out using the package of programs from UWGCG (Devereux et al., Nucl. Acids. Res. 12:387–397, 1984).

Plasmid Constructions. To construct pEG202-hsRPB7, the original JG4-4-hsRPB7 clone was digested with EcoR1 and XhoI, and cloned into the vector pEG202ATT (a derivative of pEG202 (Golemis et al., 1994, supra) modified so that the reading frame from EcoR1 corresponds to ATT, that had similarly been digested with EcoR1 and Xho I. The resulting clone encoded a fusion protein in which the LexA coding sequences were followed by the sequence NSARG-GTLPAYLVWE (Sequence I.D. No. 5) followed by the hsRPB7 coding sequences.

To construct pEG202-RPB7, oligonucleotides EG34 (5'-GGG CAA TTG GCG TCG AGA ATG TTT TTT ATT AAA GAC CTT TC)(Sequence I.D. No. 6) and EG35 (5'-CCC CTC GAG ATG TTG CGG AGT AAC AAG TGA TTA AAT A) (Sequence I.D. No. 7) were used to amplify and add a 5' Mun I site and a 3' XhoI site to $^-$540 bp containing the RPB7 coding sequence from the plasmid pRB718 (which contains a 2.8 kb genomic fragment encompassing RPB7 in the vector pGEM3Zf). This fragment was cloned into the Sma I site of pUC119, and the sequence confirmed. The fragment was then excised using MunI and XhoI, and cloned into pEG202 cut with EcoRI and XhoI, to create a fusion protein in which the C-terminal end of LexA is followed by the amino acid sequence ELASR, followed by RPB7 coding sequences. To construct the plasmid JG4-4-RPB7, used for overexpression of the yeast subunit, a MunI-XhoI fragment from the pUC119/RPB7 plasmid and cloned into JG4-4 cut with EcoRI and XhoI.

Oligonucleotides EG36 (5'-GGG CAA TTG TCG GGA AAA ATG AAT GTT TCT ACA TCA ACC) (Sequence I.D. No. 8) and EG37 (5'-CCC CTC GAG ATA CAG TTA TTA ATA GAG TGT TTC TAG G) (Sequence I.D. No. 9) were used in a similar strategy to isolate and add MunI and XhoI sites to RPB4 coding sequences, using pRP415 (which contains a 2.3 genomic fragment encompassing RPB4 in the vector YEplac181 (Gietz and Sugino 1988)) as sequence donor. After confirmation of the correct sequence, the ~620 bp of coding sequence were excised from pUC119 and inserted into EcoRI and XhoI cut JG4-5, creating an in-frame fusion protein with the SV40 nuclear localization motif, the B42 transcriptional activation domain, and the HA1 epitope tag.

The plasmid pRP729 has an ~1.4 kb RPB7 containing fragment with ~600 bp 5' BamHI ends and ~300 bp 3' SalI ends cloned into the BamHI/SalI sites of the HIS3/CEN-ARS vector pRS416 (Sikorski & Hieter, Genetics 122:19–27, 1989). pRP730 has the ~1.4 kb BamHI/SalI insert from pRP729 cloned into the BamHI/SalI sites of the URA3/CEN-ARS plasmid pRS413 (Sikorski & Hieter, 1989, supra). To construct plasmid pRP731, the RPB7 coding sequences of pRP730 were exactly replaced with those of hsRPB7 using a two step PCR method (Dillon & Rosen, Biotechniques 9:298–300, 1990). First, two sets of oligonucleotides were used to create fragments representing the S. cerevisiae RPB7 5' sequences (oligo A, 5'-GCG GAT CCG CTC CTT TCC CTG CTC TAT GCC (Sequence I.D. No. 10); oligo B, 5'-GCA GAT ATG GTA GAA CAT TCT CAG AAA TTG AG (Sequence I.D. No. 11)) and 3' sequences (oligo C, 5'-ACT TGG GGC TTG TAA GCT GAT CAC TTG TTA CTC CGC (Sequence I.D. No. 12); oligo D, 5'-GCG TCG ACG AGG GGG AAT AGA TTC TTT AGC (Sequence I.D. No. 13)) using pRP729 as a template. These two PCR fragments contained ~15 bps of sequence (underlined regions of oligos B and C) complementary to the 5' and 3' ends of the hsRPB7 gene. In the second PCR step, three overlapping fragments (the two fragments created in the first step, along with the linearized JG4-4-hsRPB7 plasmid containing the hsRPB7 coding sequence) were amplified using oligos A and D. The final PCR product containing the hsRPB7 gene flanked by S. cerevisiae RPB7 promoter and 3' sequences was then transformed into WY-73 along with gapped pRP730 (which has the RPB7 gene and part of its 5' and 3' DNA removed following digestion with SnaBI and MunI) according to Muhlrad et al. (Yeast 8:79–82, 1992). Recombination between the complementary sequences in the PCR fragment and the vector occur during transformation, yielding plasmid pRP731 in the yeast strain WY-78.

Plasmid Shuffle. The yeast strains containing the yeast RPB7 HIS3 plasmid (WY-74) and the hsRPB7 plasmid (WY-75) were obtained by selecting against the wild type RPB7 URA3 plasmid using 5-fluoroorotic acid (Boeke et al., Meth. Enz. 154:164–175, 1987). This was achieved by transferring WY-77 and WY-78 cells to a his-leu-dropout plate containing 1 mg/ml of 5-fluoroorotic acid and selecting for growth at 30° C. As a control, the same procedure was done in parallel with the yeast strain containing the control HIS3 plasmid RS413 (WY-76) to demonstrate that this plasmid alone could not support yeast cell growth at 30° C.

To confirm that the correct plasmid was being expressed in hsRPB7 cells, we rescued the plasmid from yeast cells and verified that it contained the hsRPB7 gene (and not RPB7) using PCR with gene-specific oligonucleotides.

Growth Profiles. WY-74 and WY-75 yeast were grown to saturated overnight cultures in his-leu- defined minimal medium, and re-diluted to $OD_{600}<0.05$ for growth curves. Growth curves were performed as shown in the text, with readings taken at 90 minute intervals for 12 hours, and at less frequent intervals up to 48 hours or longer. For colony formation assays in stationary phase, serial dilutions were made from the same cultures used for the growth curve, and plated YPD plates which were grown at 30° C. for 3 days, at which time colonies were counted. For tests of resistance to heat shock, cells from fresh overnights were plated onto his-leu- defined minimal plates, and grown at 42° C. for periods of 0–7 hours before being returned to 30° C. for 3 days, after which time viable colonies were counted.

Interaction Analysis. EGY48 yeast were transformed by standard methods with plasmids expressing LexA-fusions, activation-domain fusions, or both, together with the LexA operator-LacZ reporter SH18-34 (commercially and/or publically available). For all fusion proteins, synthesis of a fusion protein of the correct length in yeast was confirmed by Western blot assays of yeast extracts (Samson et al., Cell 57:1045–1052, 1989) using polyclonal antiserum specific for LexA (Brent & Ptashne, Nature 312:612–615, 1984) or for hemagglutinin (Babco, Inc.), as appropriate. LexA-RPB7 and LexA-hsRPB7 were expressed to comparable levels. Activation of the LacZ reporter was determined as previously described (Brent & Ptashne, Cell 43:729–736, 1985): beta-galactosidase assays were performed on three independent colonies, on three separate occasions, and values for particular plasmid combinations varied less than 25%. Activation of the LEU2 reporter was determined by observing the colony forming ability of yeast plated on complete minimal medium lacking leucine. The LexA-PRD/HD expressing plasmid has been described (Golemis & Brent, Mol. Cell Biol. 12:3006–3014, 1992).

Interaction Trap. EGY191 yeast containing LexA-operator-LEU2 and LexA-operator-LacZ reporter genes and expressing the LexA-hsRPB7 fusion protein was transformed with a cDNA library constructed in the vector JG4-5 such that cDNAs were expressed from the GAL1 galactose-inducible promoter as fusions to an activation domain, a nuclear localization sequence and a epitope tag derived from hemagglutinin (Gyuris et al., Cell 76:791–803, 1993; Golemis et al., 1994, supra). Preliminary results indicated that hsRPB7 met all criteria necessary to be an appropriate interaction trap probe, inasmuch as a LexA-hsRPB7 protein was stably made in EGY191 yeast, was capable of binding LexA-operator sequences, activated transcription only weakly, and had been shown to interact strongly with yeast RPB4 cloned into JG4-5. A HeLa library was used for the screen and positive clones were isolated by published methods (Golemis et al., 1994, supra).

Cell Labelling and Immunoprecipitation

WY-74 and WY-75 yeast cells were labelled with [35S] methionine for 1 hour and immuno-precipitated as described (Kolodziej & Young, Meth. Enz. 194:508–519, 1991), using 8WG16 antibody specific to the carboxy terminal domain of the RPB1 subunit (Thompson et al. 1990). Immunoprecipitated subunits were resolved by electrophoresis on a 12% SDS-polyacrylamide gel. Gels were fixed in 30% methanol, 10% glacial acetic acid, treated with Enlightning (Dupont), and exposed on Kodak AR film for 1–2 days. Additional quantitation was done using a Fuji Bioanalyzer.

Northern Analysis

The synthetic oligonucleotide EG53 (AGC AAG TTG GGG CCG AAG)(Sequence I.D. No. 14) was used as a probe for hsRPB7 expression. The synthetic oligonucleotide EG33 (CAG TTC ATC CGG ACT CAG GAC TCC G) (Sequence I.D. No. 15) was used as a probe for hsRPB1 expression. Oligos were radioactively labeled using T4 polynucleotide kinase and crude γ-32P-ATP (ICN Radiochemical). The multiple tissue Northern blots, MTN1 and MTN2, were purchased from Clontech, and had been previously normalized to within 3-fold variation of mRNA levels using an actin probe. Additionally, we have stripped and rehybridized them with a probe for another gene, HEF3, and observed less than 3-fold variation in signal intensity between lanes. Hybridizations were carried out selective temperature washes were done at 50° C. Blots were exposed on Kodak AR film at −70° C. for 2 days-10 days, and were subsequently quantitated using a Fuji Bioanalyzer.

RESULTS

Ovexpression of hsRPB7 influences S. cerevisiae cell morphology

To identify proteins that regulate the morphology and polarity of human cells, we screened a human CDNA library for genes which enhanced formation of pseudohyphae when expressed in the yeast S. cerevisiae. S. cerevisiae undergoes a dimorphic shift in response to severe nitrogen limitation that involves changes in budding pattern, cell cycle control, cell elongation, and invasive growth into agar (Gimeno et al., 1992, supra). A galactose-inducible HeLa cell cDNA library was used to transform a yeast strain that can form pseudohyphae on nitrogen-restricted media, and a number of human genes which specifically enhanced pseudohyphal formation were identified. One of the cDNAs derived from this screen was found to cause longer filamentous projections of diploid yeast grown on low-nitrogen media, and to lead to the production of a greater number of projections per microcolony. In contrast, expression of this cDNA had no effect on cell morphology in haploid yeast, or in yeast grown on rich media. Analysis of the sequence of this gene (Sequence I.D. No. 3) revealed that it was a novel human gene with strong sequence similarity to the yeast RPB7 gene (McKune et al., 1993, supra). We designated this gene hsRPB7.

HsRPB7 belongs to a closely related group of RNA polymerase subunits

The CDNA encoding hsRPB7 consisted of 775 bp including 28 bp of 5' untranslated sequence, an ATG leading into an open reading frame of 172 amino acids, and a 25 bp polyA-tail (Sequence I.D. No. 4). The predicted isoelectric point of the RPB7hs protein occurs at pH 5.3, and reflects the presence of acidic residues predominantly located at the C-terminal end of the protein. Inspection of the protein sequence reveals a number of good potential phosphorylation sites for casein kinase II (CKII), as well as two potential phosphorylation sites for protein kinase C (PKC), although whether these sites are phosphorylated in vivo remains an open question. The yeast RPB7 subunit does not appear to be phosphorylated (Kolodziej et al., 1990, supra), and diverges from hsRPB7 at most of the possible CKII and PKC consensus sites.

Comparison of the predicted hsRPB7 coding sequence to the Genbank database using the BLAST algorithm (Altschul et al., 1990, supra) revealed significant homology to a family of RNA polymerase subunits of which the most well characterized member is the yeast RPB7 subunit (McKune et al., 1993, supra). HsRPB7 possesses 43% identity (63% similarity) to the RPB7, 53% identity (76% similarity) to the fifth largest subunits of the RNA polymerases of Glycine max (soybean) and Arabidopsis (Ulmasov & Guilfoyle, J. Biol. Chem. 267:23165–23169, 1992). Comparison of the yeast, plant and human sequences also indicates that the human sequence is closer to yeast and plant than they are to each other. Although more distantly related, hsRPB7 also possessed 21% identity (48% similarity) to the yeast YKL1 gene (Abraham et al., Yeast 8:227–238, 1992), which has recently been shown to encode the C25 subunit of yeast RNA polymerase III (Sadhale & Woychik 1995, in press), and 21% identity (44% similarity) to the rpoE subunit of the archaebacterium Sulfolobus acidocaldarius (Genbank accession number X75411). The conservation of extensive homology through such an evolutionarily divergent group of organisms suggests an important function for the RPB7 family of proteins. Finally, while the sequence similarity between this group of proteins extends through the entire length of sequence, it is most pronounced in the region extending from amino acid residues ⁻70–90 of the hsRPB7 sequence. This conserved domain is essential for RPB7 and C25 function in S. cerevisiae since deletion of this region resulted in lethality (Sadhale and Woychik 1995, in press), and likely serves an important role in human cells as well.

Overexpression of RPB7 also alters S. cerevisiae cell morphology

Because the isolation of a polymerase subunit homolog was initially surprising in a screen for regulators of cell morphology, to verify the physiological significance of our finding we tested whether overexpression of the yeast RPB7 gene would similarly enhance pseudohyphal formation. We overexpressed the yeast RPB7 gene from the same galactose-inducible expression vector used to clone hsRPB7, and compared pseudohyphal formation by hsRPB7, RPB7, or vector-containing CGx74. Cell elongation and adaptation of a unipolar budding pattern was notably more pronounced with the yeast RPB7 than with the human hsRPB7, suggesting that the phenotype was not the result of hsRPB7 interfering with RPB7 function. Overexpression of neither hsRPB7 nor RPB7 resulted in decreased viability or growth rate of yeast.

HsRPB7 can complement RPB7 deletion strains at moderate temperatures

Since the amino acid sequence of the hsRPB7 protein is well conserved from humans to yeast, we wanted to determine if hsRPB7 can functionally substitute for S. cerevisiae RPB7. Using the plasmid shuffle method (Boeke et al., 1987, supra), we tested if expression of hsRPB7 was able to rescue the lethality associated with an RPB7 null mutation (McKune et al., 1993, supra). Yeast cells that have the chromosomal copy of RPB7 disrupted by insertion of the LEU2 gene plus a wild type complementing copy of the RPB7 gene on a URA3 plasmid were transformed with an additional HIS3 plasmid, containing either hsRPB7 under the control of the RPB7 promoter or the RPB7 gene and its promoter. Ura+His+Leu+transformants were transferred to media containing 5-fluoroorotic acid to select for loss of the yeast RPB7 /URA3 plasmid. Both the yeast RPB7 control plasmid and the hsRPB7 plasmid supported wild type levels of yeast cell growth at moderate temperatures, indicating that the human RPB7 homolog can functionally replace its yeast counterpart under these growth conditions.

HsRPB7-dependent yeast cells are temperature sensitive, cold sensitive and have stationary phase defects Induction of pseudohyphal growth occurs in response to nutritional stress (ie, nitrogen restriction). We tested the growth of yeast containing hsRPB7 in response to other stressors, including high temperature, low temperature, heat shock, and maintenance at stationary phase. In contrast to their growth at moderate temperatures, yeast cells expressing hsRPB7 possessed phenotypes strikingly different from wild type yeast when cultured at high and low temperatures, or when continuously cultured after reaching stationary phase. After shifting cells from 30° C. to 37° C., yeast expressing hsRPB7 grow through early and mid-logarithmic phase at essentially the same rate as wild type yeast. As they enter late log phase, the growth rate of hsRPB7 cultures is somewhat reduced relative to that of wild type yeast, and cultures saturate at lower levels. Observation of the cells in the hsRPB7 and RPB7 cultures at 37° C. indicated that while cells in both cultures rapidly became morphologically abnormal, with many cells developing vacuoles, "bumpy" cell walls, and misformed buds, the abnormalities were more severe in yeast containing hsRPB7. Removal and replating of equivalent numbers of cells from stationary phase cultures of hsRPB7 and RPB7 yeast grown at 37° C. and 30° C. indicated that hsRPB7 yeast lost viability significantly more rapidly than RPB7 yeast at both temperatures, with the difference most pronounced at 37° C. Finally, hsRPB7 yeast also grew more poorly than RPB7 yeast at 12° C., although the difference was less pronounced.

RPB7 has been shown to form a highly stable subcomplex with the yeast RPB4 subunit (Edwards et al., J. Biol. Chem. 266:71–75 1991; Young, 1991, supra). This subcomplex appears to play a key role in enabling yeast survival during periods of stress and during stationary phase (Choder, J. Bact. 175:6358–6363, 1993; Choder & Young, Mol. Cell Biol. 13:6984–6991, 1993). The defects seen in hsRPB7 yeast cells, including conditional lethality at high and low temperatures and stationary phase defects, were similar to those seen with rpb4$^-$ mutations (Choder & Young, 1993, supra). We tested an additional parameter associated with the lack of the RPB4 gene, reduced resistance to heat shock (Choder & Young, 1993, supra). Cultures of hsRPB7 and RPB7 expressing yeast were grown at 30° C., then exposed to timed heat shock at 42° C. Yeast expressing RPB7 remained fully viable for at least 7 hours at 42° C., whereas yeast expressing hsRPB7 rapidly lost viability and became completely inviable between 3 and 5 hours of heat shock.

HsRPB7 associates with yeast RPB4 and hsRPB4 associates with yeast RPB7

The above data indicated that hsRPB7 could complement the essential function of RPB7, but might be deficient in its ability to interact with RPB4 or another protein in the transcription complex. To directly test this hypothesis, we utilized a two hybrid interaction trap approach (Fields & Song, Nature 340:245–246, 1989; Gyuris et al., 1993, supra; Golemis et al., 1994, supra). We used the constitutive ADH promoter to express hsRPB7 and RPB7 as fusions to the DNA binding protein LexA, and the galactose-inducible GAL1 promoter to express RPB4 as a fusion to a transcriptional activation domain. We transformed these constructions and a negative control (LexA fused to the PRD box and homeodomain of bicoid (Gyuris et al., 1993, supra)) together with a LexA operator-LacZ reporter into yeast, and compared activation of the reporter by LexA-RPB7, LexA-hsRPB7, and LexA-PRD/HD in the presence or the absence of the activation domain-fused RPB4 protein. Both RPB7hs and RPB7 interacted with RPB4 in yeast, while the negative control protein did not. However, the degree of enhancement of activation as quantitated by β-galactosidase assay was considerably greater for the RPB4-RPB7 combination than for the hsRPB7-RPB4 combination (60 fold versus 2–3 fold), suggesting that the $K_d$ of association is much greater for the two yeast proteins. These results indicate that hsRPB7 is able to interact with yeast RPB4 in vivo, but does so at with a lower affinity than the RPB4-RPB7 subunit pair.

Experiments similar to those described above were performed with hsRPB4 protein and yeast RPB7. Results of those experiments likewise indicated that hsRPB4 is able to interact with yeast RPB7 in vivo, but with a lower affinity than the yeast RPB4-RPB7 pair.

HsRPB7 assembles with yeast RNA Polymerase II subunits

Previous work has shown that RPB7 does not appear to associate with RNA pol II in yeast lacking RPB4 (Kolodziej et al., 1990, supra). Because rpb7$^-$ yeast are inviable, it has been impossible to determine whether RPB7 is required for RPB4 to associate with RNA pol II. As our data indicated that hsRPB7 associated poorly with RPB4, one possible explanation for the rpb4-like defects of hsRPB7 yeast was that RPB4/hsRPB7 were unable to assemble with the remainder of the pol II subunits. To test this possibility, we immunoprecipitated 35S-labelled pol II from RPB7 or hsRPB7 expressing yeast using an antibody to the carboxy terminal domain of the largest subunit of pol II, resolving individual subunits by SDS-PAGE. Quantitation of the stoichiometry of precipitated subunits from the two species was identical, indicating that hsRPB7 is able to assemble with the full set of yeast pol II subunits, including RPB4.

Tissue-specific expression of hsRPB7 and hsRPB4 RNA

We examined the expression levels of hsRPB7 and hsRPB4 mRNA in different human tissues using Northern blot analysis. The hsRPB7 probe hybridized to a single band of approximately 800 bp, which together with the presence of homology to the full length of RPB7 coding sequence indicates the hsRPB7 cDNA isolated in the screen is full length or close to full length. The hsRPB4 probe hybridized to a 1.8 kb band and to a 4 kb band.

Surprisingly, the hsRPB7 mRNA fluctuated drastically between tissues, being expressed at very high steady-state levels in heart, muscle, kidney, and liver, and at much lower levels in other tissues. Direct quantitation of 32P label using a Fuji Bioanalyzer indicated as much as an 80–90 - fold variation between high and low end values.

This difference in steady-state hsRPB7 mRNA levels could reflect the abundance of transcripts encoding pol II subunits, or it could reflect differential levels of the hsRPB7 mRNA relative to the rest of the complex. To resolve these two possibilities, we stripped the multitissue blot and rehybridized with a probe specific for the largest subunit of human RNA pol II (Wintzerith et al., Nucl. Acids Res., 20:910, 1992), here designated hsRPB1. This probe hybridized specifically to a single transcript of ~6.7 kb, corresponding to the reported size of the transcript encoding this subunit (Wintzerith et al., 1992, supra), that was present at similar levels in all tissues examined, and to a single transcript of ~7.5–8 kb unique to placental tissue, that might represent an alternately spliced form of the gene encoding the largest subunit. Strikingly, the steady-state levels of the hsRPB1transcript differ substantially in tissue distribution relative to the hsRPB7 transcript. While levels of hsRPB1 were somewhat elevated in kidney and muscle (although much less that the hsRPB7 transcript), they were extremely low in liver and heart. These data suggest that transcription or stability of the hsRPB7 mRNA is regulated differently than that of the largest pol II subunit, and imply that hsRPB7 might be differentially available to RNA polymerase II in different tissues.

Experiments with hsRPB4 also indicate that hsRPB4 is differentially expressed in different tissues. HsRPB4 mRNA was expressed at high steady-state levels in heart and muscle, relative to other tissues.

Characterization of hsRPB4 cDNAs isolated by Interaction Trap

One cDNA was isolated five times in the interaction trap screen. The nucleotide sequence of this cDNA corresponds approximately to nucleotides 62 to the end of Sequence I.D.

No. 1. Comparison of the deduced amino acid sequence of the longest open reading frame from this sequence to the GENBANK protein database indicated a probable relationship with two proteins. One was the yeast RPB4 protein; another was a protein sequence from chicken.

From the sequence comparison, the cDNA was positively identified as a human RPB4 homolog, which was designated hsRPB4. The nucleic acid sequence of a hsRPB4 was used to re-screen GENBANK to identify any additional amino terminal sequences of hsRPB4. This led to the identification of a partially sequenced cDNA (c11eO2 Accession No. z43809) which, when merged with the sequence of hsRPB4, yielded the nucleotide sequence set forth as sequence I.D. No. 1 and the protein sequence set forth as sequence I.D. No. 2. Sequence I.D. No. 1 is believed to constitute a full-length hsRPB4 clone, since it contains a suitable methionine for initiation of translation and it encodes a transcript of about the same size. The cloned sequence is approximately 1.8 kb. Northern analysis of a human multi-tissue RNA blot (Clontech) with the hsRPB4 probe suggests that one full length transcript is approximately 1.8–2.1 kb. A second transcript of about 4 kb was also observed, which could be an alternate splice/initiation site or could encode a related protein. Amino acid Sequence I.D. No. 2 contains statistically significant homology to another protein in the GENBANK database, a chicken protein of unknown function, which also may play an RPB4-like role or may be a different, but related, transcription factor. Sequence I.D. No. 1 is about 40% identical to the coding sequence of the yeast RPB4. Sequence I.D. No. 2 shares about 31% identity and 51% similarity to the yeast RPB4 coding amino acid sequence. It is expected that greater sequence homolgies will be found between hsRPB4 and RPB4 of more closely related species (i.e., mammals, particularly primates).

DISCUSSION

After identifying the hsRPB7 gene using a screen for proteins which influence yeast cell morphology, we established that at least part of the RPB7 function has been conserved through humans, to the extent that hsRPB7 expression can rescue the lethality of an rpb7- deletions. However, yeast expressing the hsRPB7 subunit have significantly altered growth properties relative to yeast expressing RPB7, particularly under extreme growth conditions, which is likely due to a reduced ability to associate with the yeast RPB4 subunit. We have found that both hsRPB7 and RPB7 are able to enhance formation of pseudohyphae in yeast, implying an unexpected connection between a core element of the yeast transcription apparatus and a change in cell growth control. The fact that the expression pattern of hsRPB7 in humans is highly variable between different tissues suggests this subunit may play a regulatory role, but this remains to be established.

Human homologs have been reported previously for a number of the twelve subunits of the S. cerevisiae RNA polymerase II (Cho et al., J. Biol. Chem. 260:15204–15210, 1985; Pati & Weissman, J. Biol. Chem. 264:13114–13121, 1989; Pati & Weissman, J. Biol. Chem. 265:8400–8403, 1990; Acker et al., Nucl. Acids Res. 21:5345–5350, 1993; McKune & Woychik, Mol. Cell. Biol. 14:4155–4159, 1994). In general, the degree of evolutionary sequence conservation is quite high for all the subunits so far cloned. Of subunits tested to date, the human homolog has been able to at least partially complement the yeast equivalent in five cases (including hsRPB7) and not been able to in two others (e.g., McKune et al. 1993, supra). Results from the two-hybrid and co-precipitation experiments described here suggest a mechanism for the conditional complementation phenotype of hsRPB7. Pol II from yeast growing under the control of hsRPB7 contains levels of RPB4 and hsRPB7 similar to wild type yeast: However, hsRPB7 and RPB4 appear to interact much more poorly than RPB7 and RPB4, indicating the two may not associate together appropriately. Thus, under normal growth conditions in which RPB4 function is not necessary, hsRPB7 can fulfill the essential function of RPB7. Under stressful growth conditions, RPB4 is unable to execute its protective function in concert with hsRPB7. These data imply that a human RPB4 homolog, if it exists, diverges significantly in sequence from the yeast RPB4 gene. Alternatively, hsRPB7 may associate with different cellular factors entirely, that may or may not be involved in cellular stress response. Finally, immunoprecipitation of RNA polymerase II from extracts prepared from cells lacking RPB4 revealed that RPB7 is also not visible (Kolodziej et al., 1990, supra), suggesting that RPB4 is required for a stable association of RPB7 with pol II. Our data imply that RPB4 may not require its interaction with RPB7 to associate with the polymerase, a point which it had previously been impossible to test because of the lethality of rpb7-mutations.

Two-hybrid analysis revealed that, although hsRPB7 and yeast RPB4 interact, the association is of lower affinity than the yeast RPB4-RPB7 interaction. Characterization of the hsRPB4 CDNA shows a comparatively low sequence homology with yeast RPB7, suggesting structural non-similarities between the two RPB4 proteins that could explain the low affinities of hsRPB7 for yeast RPB4 and of hsRPB4 for yeast RPB7. However, the high frequency of obtaining the hsRPB4-encoding cDNA in the interaction trap screen indicates that hsRPB4 is likely to associate with a comparably high affinity to hsRPB7, as does yeast RPB4 to yeast RPB7. Taken together, these data indicate that the hsRPB4/hsRPB7 subcomplex of RNA pol II functions in a manner similar to the same complex in yeast, with the RPB4 subunit being the stress-inducible component of the subcomplex.

The present invention is not limited to the embodiments specifically described above, but is capable of variation and modification without departure from the scope of the appended claims.

What is claimed is:

1. An isolated nucleic acid molecule that includes a sequence encoding an RPB4 subunit of human RNA polymerase II.

2. The nucleic acid molecule of claim 1, which is DNA.

3. The nucleic acid molecule of claim 1, which is RNA.

4. An oligonucleotide between about 10 and 100 nucleotides in length, which is complementary to a portion of the sequence of claim 1, said portion including a translation initiation site of said RPB4 subunit.

5. The nucleic acid molecule of claim 1, wherein said sequence encodes a polypeptide 142 amino acids in length.

6. The nucleic acid molecule of claim 1, wherein said sequence encodes a polypeptide having an amino acid sequence selected from the group consisting of:
    (a) Sequence I.D. No. 2;
    (b) an allelic variant of Sequence I.D. No. 2; and
    (c) a sequence having conservative amino acid substitutions in Sequence I.D. No. 2 that are not involved in function of said polypeptide.

7. The nucleic acid molecule of claim 6, wherein said sequence encodes amino acid sequence I.D. No. 2.

8. The nucleic acid molecule of claim 7, wherein said sequence is Sequence I.D. No. 1.

9. An isolated nucleic acid molecule comprising a sequence selected from the group consisting of:

(a) Sequence I.D. No. 1;

(b) an allelic variant of Sequence I.D. No. 1; and (c) a sequence encoding a polypeptide having amino acid Sequence I.D. No. 2.

10. The nucleic acid molecule of claim 9, which is DNA.

11. The nucleic acid molecule of claim 9, which is RNA.

* * * * *